United States Patent
Kenalty et al.

(10) Patent No.: US 8,672,842 B2
(45) Date of Patent: Mar. 18, 2014

(54) SMART MATTRESS

(75) Inventors: Christopher Kenalty, Toronto (CA); Miriam Gordon, Mississauga (CA); Hart Victor Katz, Toronto (CA)

(73) Assignee: Evacusled Inc. (CA)

( * ) Notice: Subject to any disclaimer, the term of this patent is extended or adjusted under 35 U.S.C. 154(b) by 110 days.

(21) Appl. No.: 13/215,703

(22) Filed: Aug. 23, 2011

(65) Prior Publication Data
US 2012/0053424 A1    Mar. 1, 2012

Related U.S. Application Data

(63) Continuation-in-part of application No. 12/862,253, filed on Aug. 24, 2010.

(51) Int. Cl.
| | |
|---|---|
| *A61B 5/00* | (2006.01) |
| *A61B 5/0205* | (2006.01) |
| *A61B 6/04* | (2006.01) |
| *A47C 27/00* | (2006.01) |
| *G01L 15/00* | (2006.01) |
| *G01L 19/00* | (2006.01) |

(52) U.S. Cl.
CPC ............ *A61B 5/0002* (2013.01); *A61B 5/0205* (2013.01); *A61B 6/0407* (2013.01); *A47C 27/002* (2013.01); *G01L 15/00* (2013.01); *G01L 19/0092* (2013.01); *G01L 2019/0053* (2013.01); *A61B 2505/00* (2013.01); *A61B 2560/0468* (2013.01); *A61B 2562/0247* (2013.01)
USPC ... 600/300; 600/587; 340/573.1; 340/539.12; 5/499; 324/691; 73/862.046; 73/172; 702/47; 702/138; 702/139

(58) Field of Classification Search
USPC ...................................... 5/600–624
See application file for complete search history.

(56) References Cited

U.S. PATENT DOCUMENTS 4,033,332 A * 7/1977 Hardway et al. ............... 600/535
4,484,043 A * 11/1984 Musick et al. ............... 200/85 R (Continued)

FOREIGN PATENT DOCUMENTS

WO    WO2011077326 A2 * 12/2012

OTHER PUBLICATIONS

Transmittal; International Search Report; and the Written Opinion of the International Searching Authority for International Application No. PCT/IB2011/002638 with mailing date of Apr. 17, 2012.

*Primary Examiner* — Bill Thomson
*Assistant Examiner* — Marie Archer
(74) *Attorney, Agent, or Firm* — Katten Muchin Rosenman LLP

(57) ABSTRACT

A mattress has a sensor pad affixed on a top surface thereof. The sensor pad has (i) a matrix array of plural pressure sensors, (ii) plural row conductors, and (iii) plural column conductors. Each intersecting row and column conductor provides an electrical signal from a corresponding sensor when pressure is applied thereto. The sensor pad has plural throughholes therein disposed between the plural row conductors the plural column conductors, respectively. Preferably, at least one patient-mounted physiological sensor is configured to provide an output signal corresponding to a patient physiological parameter. An electronic unit is mounted inside the mattress and is configured to receive signals from the sensor pad. The electronic unit has a data storage unit preferably storing (i) patient identification information, (ii) patient physiological information, and (iii) mattress information. A wireless transmitter is coupled to the electronic unit and is configured to wirelessly communicate at least the stored patient physiological information to an off-mattress device.

12 Claims, 12 Drawing Sheets

(56) References Cited

U.S. PATENT DOCUMENTS

| | | | |
|---|---|---|---|
| 4,633,237 A | 12/1986 | Tucknott et al. | |
| 4,862,144 A | 8/1989 | Tao | |
| 5,010,772 A * | 4/1991 | Bourland et al. | 73/862.046 |
| 5,086,291 A * | 2/1992 | Schwab, Jr. | 340/604 |
| 5,137,033 A * | 8/1992 | Norton | 128/886 |
| 5,144,284 A * | 9/1992 | Hammett | 340/573.1 |
| 5,249,321 A | 10/1993 | Graf | |
| 5,253,656 A * | 10/1993 | Rincoe et al. | 600/595 |
| 5,410,297 A * | 4/1995 | Joseph et al. | 340/573.7 |
| 5,448,996 A * | 9/1995 | Bellin et al. | 600/574 |
| 5,590,650 A | 1/1997 | Genova | |
| 5,844,488 A | 12/1998 | Musick | |
| 5,882,300 A | 3/1999 | Malinouskas et al. | |
| 6,307,168 B1 * | 10/2001 | Newham | 200/86 R |
| 6,485,441 B2 | 11/2002 | Woodward | |
| 6,984,207 B1 | 1/2006 | Sullivan et al. | |
| 7,107,642 B2 | 9/2006 | Wong et al. | |
| 7,164,941 B2 | 1/2007 | Misczynski et al. | |
| 7,245,956 B2 * | 7/2007 | Matthews et al. | 600/382 |
| 7,541,935 B2 | 6/2009 | Dring et al. | |
| 7,644,459 B1 | 1/2010 | Olson | |
| 7,652,581 B2 | 1/2010 | Gentry et al. | |
| 7,785,257 B2 * | 8/2010 | Mack et al. | 600/300 |
| 7,845,035 B2 * | 12/2010 | Letton et al. | 5/727 |
| 8,161,826 B1 * | 4/2012 | Taylor | 73/862.044 |
| 8,245,341 B2 * | 8/2012 | Oh | 5/727 |
| 2002/0007124 A1 | 1/2002 | Woodward | |
| 2002/0194934 A1 * | 12/2002 | Taylor | 73/862.046 |
| 2004/0111045 A1 * | 6/2004 | Sullivan et al. | 600/595 |
| 2004/0226099 A1 * | 11/2004 | Pearce | 5/655.5 |
| 2005/0124864 A1 | 6/2005 | Mack | |
| 2005/0190068 A1 * | 9/2005 | Gentry et al. | 340/665 |
| 2006/0264785 A1 | 11/2006 | Dring et al. | |
| 2006/0271207 A1 | 11/2006 | Shaw | |
| 2007/0149883 A1 | 6/2007 | Yesha | |
| 2008/0141460 A1 | 6/2008 | Shaw | |
| 2008/0275314 A1 * | 11/2008 | Mack et al. | 600/301 |
| 2009/0056027 A1 * | 3/2009 | Ball et al. | 5/690 |
| 2009/0070939 A1 * | 3/2009 | Hann | 5/652.1 |
| 2009/0119843 A1 * | 5/2009 | Rodgers et al. | 5/611 |
| 2010/0057543 A1 | 3/2010 | Dring et al. | |
| 2010/0064439 A1 | 3/2010 | Soltani | |
| 2010/0101022 A1 * | 4/2010 | Riley et al. | 5/600 |
| 2011/0185504 A1 | 8/2011 | Kenalty et al. | |
| 2011/0224510 A1 * | 9/2011 | Oakhill | 600/301 |
| 2011/0308015 A1 * | 12/2011 | Newham | 5/499 |
| 2012/0184862 A1 * | 7/2012 | Foo et al. | 600/508 |
| 2012/0215076 A1 * | 8/2012 | Yang et al. | 600/301 |
| 2012/0277637 A1 * | 11/2012 | Vahdatpour et al. | 600/595 |
| 2012/0283979 A1 * | 11/2012 | Bruekers et al. | 702/104 |
| 2012/0323501 A1 * | 12/2012 | Sarrafzadeh et al. | 702/41 |

* cited by examiner

SMART MATTRESS

This application is a Continuation-In-Part of U.S. patent application Ser. No. 12/862,253, filed Aug. 24, 2010, the entire contents of which are incorporated herein by reference.

Reference is hereby made to the computer program listing appendix submitted herewith. The material in the appendix is hereby incorporation-by-reference in the specification. One appendix is submitted herewith and includes files: Acquisition Thread; PadGenerator; Patient; Program; SMatrix; AvgGraph Designer; AvgGraph; BasePane Designer; BasePane; BodyMap Designer; BodyMap; LogCntrl Designer; LogCntrl; Pane Caption Designer; PaneCaption; Patient Ctrl Designer; PatientCtrl; DesignGridForm Designer; DesignGridForm; FormMain Designer; FormMain; PatientForm Designer; PatientForm; FileList; AssemblyInfo; Resources.Designer; and Settings.Designer

TECHNICAL FIELD

The present invention relates to a Smart Mattress for the real-time medical monitoring of individuals such as hospital patients, bed-ridden patients, and infants susceptible to Sudden Infant Death Syndrome (SIDS). More particularly, the invention relates to such a mattress which is capable of measuring and reporting (locally or remotely) a patient's vitals and other information to a server and/or caregiver during emergency and non-emergency situations.

BACKGROUND INFORMATION

There are a number of existing methods and apparatuses which are capable of providing for real-time monitoring of a patient's vital statistics ("vitals"). These apparatuses include electrocardiogram recorders, heart rate monitors, blood pressure monitors, electroencephalograph apparatus, pulse monitors, oximeters, carbon dioxide meters, thermostats, scales, maternal uterine activity monitors, and various other noninvasive medical instruments.

A major concern with current noninvasive medical instruments is that they are often bulky and require an excessive number of cables in order to report the measurements to a computer or physician. Everyone is familiar with the image of a hospital patient excessively wired to many machines surrounding or attached to the patient's bed. Access to such patients is difficult during normal treatment, but becomes a real problem in emergency situations where rapid evacuation may be required. In emergencies, non-ambulatory or bed-ridden patients must be quickly and safely evacuated from hospitals, a situation in which patients wait (often for hours in a parking lot) for transportation to another hospital. In such emergencies, because of the issues mentioned above, most current medical instrumentation cannot be quickly and effectively packed up to preserve substantially uninterrupted patient monitoring. Similarly, in the case of home health care, it would be highly desirable to simplify and/or create more user-friendly monitoring methods by reducing the amount of equipment and creating a self-contained, maintenance-free monitoring device.

Numerous improvements in the medical field have been made to reduce the number of monitors physically attached to a patient, and the size and number of devices in a hospital room, by integrating certain sensor devices into the existing bedding of a patient. The following patents and patent publications, which are hereby incorporated by reference in their entirety herein, disclose a number of contactless, non-invasive patient monitoring methods.

A mattress pad disclosed in U.S. Patent Publication No. 20070149883 to Yesha has at least two pressure-sensitive piezoelectric sensors positioned in a rigid pad beneath the patient's mattress. The mattress pad includes a processor to receive successive sensor measurements and calculate heart and respiration rates, which are determined by subtracting the pressure signals corresponding to the upper body and the lower body of a patient and mathematically determining the maximum difference of signals between each group of sensors. The heart and respiration rates are then transmitted by a cable to existing patient monitoring equipment. This system, however, requires that a rigid pad be properly disposed and positioned beneath the mattress while physically connected to an auxiliary device, restricting both the mobility and versatility of the monitoring system.

A mattress with integrated piezoelectric sensors disclosed in U.S. Pat. No. 7,652,581 to Gentry has a passive sensor, or sensor array, in the mattress pad that supports continuous monitoring of a patient's physiological condition in a hospital setting. The external processor receives sensor data, either by wired or wireless communication, from mattress pad sensors, and processes the sensed data into a form that is usable by a physician, nurse or other user. As in Yesha, this is not a self-contained monitoring mattress and still requires auxiliary equipment to receive and process sensor data.

Yet another monitoring mattress pad apparatus is disclosed in U.S. Pat. No. 7,164,941 to Misczynski. This document discloses a contactless electromagnetic inductance device which collects cardiac activity signals to evaluate patient sleep. As in Yesha, the system is not self-contained and also does not permit storage of patient data.

There are numerous other patents and published patent applications which employ a pad or embedded mattress sensor coupled to an auxiliary device. One apparent disadvantage is the lack of a self-contained system and the reliance on or requirement of an auxiliary device. Another disadvantage is the lack of embedded storage for patient identification and other data, such as a patient's chart information.

Thus, what is needed is a self-contained Smart Mattress which is capable of monitoring vital statistics of a patient in real time, analyzing data using an embedded processor, storing patient identification and medical information, producing an electronic medical report, and communicating pertinent data to a caregiver or computer server using wireless technology, such as Bluetooth® Technology. Due to the self-contained, portable nature of the Smart Mattress and Smart Mattress technology, it is also ideal for use with an emergency evacuation mattress system for hospital patients and other bed-ridden patients.

SUMMARY

Health care providers are very mobile, and the adoption of enhanced wireless technology by health care organizations, especially when harnessed properly, can help to improve, even automate, patient care and monitoring, save costs, and reduce staff injuries. It is indisputable that computer networks are commonplace in health care organizations and in some places are indispensable. However, most of the computer devices and monitoring devices are connected through the use of wires; this usually means that their use is limited to a fixed place. A Smart Mattress eliminates many of the wires associated with current methods and allows for greater flexibility in patient monitoring.

According to a first aspect of the present invention, a mattress has a non-rigid, flexible sensor pad affixed on a top surface thereof. The sensor pad has (i) a matrix array of plural pressure sensors, (ii) plural row conductors, and (iii) plural column conductors. Each intersecting row and column conductor provides an electrical signal from a corresponding sensor when pressure is applied thereto. The sensor pad having plural through-holes therein disposed between the plural row conductors the plural column conductors. A connector is preferably coupled to outputs of the row and column conductors. Preferably, at least one patient-mounted physiological sensor is configured to provide an output signal corresponding to a patient physiological parameter. An electronic unit is mounted inside the mattress and preferably has a panel mounted on a side of the mattress. The panel is configured to receive signals from the connector. The electronic unit has a data storage unit preferably storing (i) patient identification information, (ii) patient physiological information, and (iii) mattress/bed information. The electronic unit receives signals from at least one patient-mounted physiological sensor. A wireless transmitter is coupled to the electronic unit and is configured to wirelessly communicate at least the stored patient physiological information to an off-mattress device.

According to a second aspect of the present invention, a Sudden Infant Death Syndrome-detecting mattress includes a sensor pad affixed on a top surface of the mattress. The sensor pad having (i) a matrix array of plural pressure sensors, (ii) plural row conductors, and (iii) plural column conductors. Each intersecting row and column conductor is configured to provide an electrical signal from a corresponding sensor when pressure is applied thereto. The sensor pad has plural through-holes therein disposed between the plural row conductors the plural column conductors. An electronic unit is mounted inside the mattress and is configured to receive signals from the row and column conductors. The electronic unit has a processor for receiving the received signals and providing al alarm signal when an infant on the mattress has stopped breathing for a predetermined period of time.

According to a third aspect of the present invention, a method of sensing physiological information of a patient lying on a mattress, includes providing a sensor pad affixed on a top surface of the mattress, the sensor pad having (i) a matrix array of plural pressure sensors, (ii) plural row conductors, and (iii) plural column conductors. The sensor pad has plural through-holes therein disposed between the plural row conductors the plural column conductors, respectively. Each intersecting row and column conductor providing an electrical signal from a corresponding sensor when pressure is applied thereto. An electronic unit is provided inside the mattress, and has a data storage unit storing (i) patient identification information, (ii) patient physiological information, and (iii) mattress/bed information. The electronic unit receives signals from the sensor pad, and has a processor. A wireless transmitter is coupled to the electronic unit, and wirelessly communicates at least the stored patient physiological information to an off-mattress device.

DETAILED DESCRIPTION OF THE PRESENTLY PREFERRED EXEMPLARY EMBODIMENTS

Figure 1:
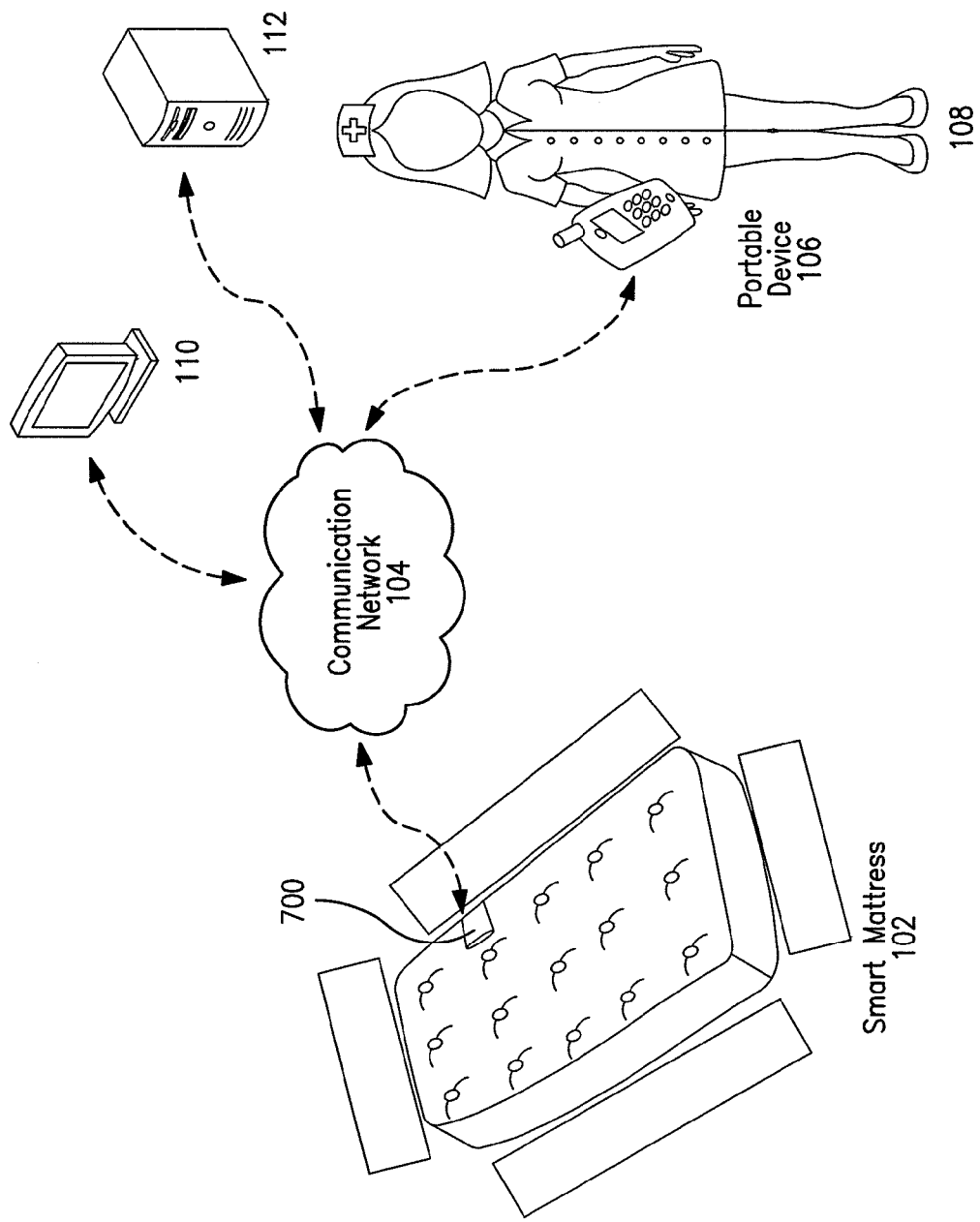
FIG. 1 is a high-level diagram illustrating a first embodiment for using Smart Mattress.

A preferred embodiment of the present invention will be described herein below with reference to the accompanying drawings. In the following description, well-known functions or constructions are not described in detail since they would obscure the invention in unnecessary detail.

For this application the following terms and definitions shall apply:

The terms "communicate" and "communicating" as used herein include both conveying data from a source to a destination and delivering data to a communications medium, system, channel, network, device, wire, cable, fiber, circuit and/or link to be conveyed to a destination, and the term "communication" as used herein means data so conveyed or delivered. The term "communications" as used herein includes one or more of a communications medium, system, channel, network, device, wire, cable, fiber, circuit and link.

The term "processor" as used herein means non-transitory processing devices, apparatus, circuits, components, systems and subsystems, whether implemented in hardware, or a combination of hardware and software, and whether or not programmable. The term "processor" as used herein includes, but is not limited to, one or more computers, hardwired circuits, signal modifying devices and systems, devices and machines for controlling systems, central processing units, programmable devices and systems, field-programmable gate arrays, application-specific integrated circuits, systems on a chip, systems comprising discrete elements and/or circuits, state machines, virtual machines, data processors, processing facilities and combinations of any of the foregoing.

The present disclosure endeavors to provide a Smart Mattress and/or Smart Mattress system capable of monitoring the vital statistics of a patient in real time, analyzing the data using an embedded processor, storing patient identification and information and mattress and/or bed information (where the bed comprises a mattress and the frame), producing an electronic medical report, and communicating any data to a care provider, computer server, or portable device using wireless technology. A portable device may be a cell phone, smart phone, Personal Digital Assistant ("PDA"), media player/reader, computer laptop, tablet PC, or any other processor-based device that is known in the art, including a desktop PC and/or computer workstation. Using a portable device allows for more flexibility when monitoring a patient or during emergency evacuations by allowing the health care provider to monitor from a distance or to receive automatic alerts when a patient's condition changes.

Integrating a Smart Mattress with a hand-held device in an emergency evacuation system has not been done, to the knowledge of the inventors. Use of a Smart Mattress alone or in combination with a portable device will enhance data collection during both day-to-day monitoring at home or in a health care facility, or while in emergency evacuations. Use of a Smart Mattress improves data accuracy, reduces paperwork, supports collection of more complete information, updates critical information faster, eliminates redundant data entry, allows faster adaptation to changing conditions and provides access to previously unavailable information. Additionally, when a patient is transferred to an alternate facility, patient records, which may be stored in a Smart Mattress data storage unit ("DSU"), travel with the patient.

1. Structure

Referring now to FIG. 1, a Smart Mattress 102 system is depicted. The Smart Mattress 102 system of FIG. 1 uses a communication network 104 to wirelessly transmit a patient's physiologic data, and/or dynamic patient data, and/or patient demographic data, and/or mattress data from a breakout unit 700 in the mattress 102 to portable device 106, monitoring station 110, and/or other computer server 112. The portable device 106 may be carried by a health care provider 108 or other personnel interested in the health of a patient. A monitoring station 110 may be either a local in-hospital nurses' station or a remote monitoring station. Alternatively, patient data may be communicated to a computer server 112 which may be capable of automatically monitoring a patient's health state or forwarding dynamic patient data to one or more health care personnel, for example, if a patient's health condition deviates from a predetermined value. Preferably, all data communication to/from the Smart Mattress is encoded (to comply with HIPPA requirements) and compressed; and all servers, communication devices, and memory devices are HIPPA-compliant. The breakout unit 700 is preferably embedded in the mattress with a connector panel on an outer surface thereof (See FIGS. 6 and 7). The breakout unit 700 is preferably mounted inside the mattress in a rigid or semi-rigid enclosure having one or more rack/slide/drawer structures, to make replacement and/or repair of the breakout unit 700 simple. Also, it is preferred that the breakout unit enclosure be waterproof and/or RFI-shielded.

Figure 7:
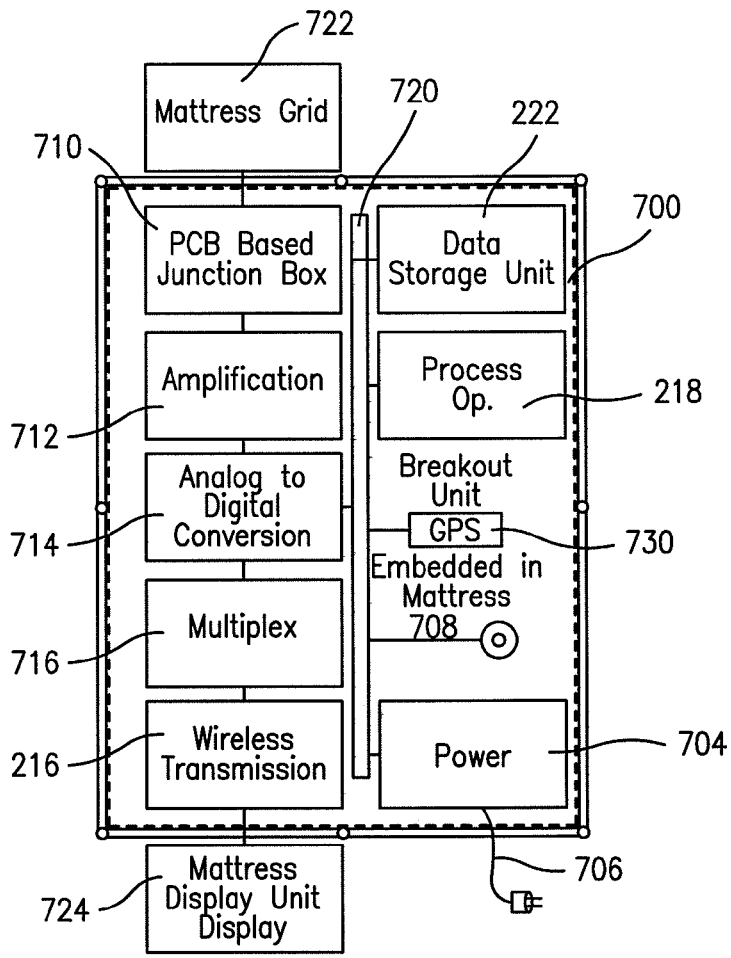
FIG. 7 is a schematic diagram of the breakout unit preferably embedded in the mattress.

In FIG. 7, the breakout unit 700 preferably includes a data storage unit ("DSU") 222 for storing patient information (e.g., demographics such as name, height, weight, gender, date of birth, race, religion and blood type), for storing and automatically updating a patient's physiological data (e.g., body temperature, systolic and diastolic blood pressures, pulse, respiratory, pulse oximetry and electrocardiogram), for storing mattress and/or bed information; and a processor for handling, processing and/or time-stamping any updates to the DSU. The DSU 222 may be removable and/or may include permanent memory together with a removable memory such as a flash drive, EEPROM, SD card, etc. In a preferred embodiment, the breakout unit 700 also includes an on-board power source 704, such as one or more rechargeable batteries, to increase the portability of a Smart Mattress and/or provide power backup in case of emergencies. Preferably, the Smart Mattress is also capable of receiving operating and/or recharging power directly from an auxiliary power source (e.g., wall socket, solar panel, and/or generator) via cable 706. The breakout unit 700 may also include a call button 708 which signals to the caregiver 108 that assistance is needed (e.g. via the portable device 106, monitoring station 110, and/or audible alarm). The breakout unit 700 may also include a GPS transmitter and/or receiver 730 to provide accurate location information for emergency or routine transportation.

The breakout unit 700 also preferably includes an on/off switch 709, and a PCB-based junction box 710 which will accept the high density of incoming wires from the sensor arrays (to be described below). Amplifier circuitry 712 is also provided to amplify the incoming sensor signals. An Analog/Digital conversion unit 714 performs typical A/D functions and preferably converts the sensor array signals at least once every minute (although the frequency of scanning and, thus, conversion may vary depending on the condition being monitored). Each sensor in the array may be sampled once every 10 seconds—i.e., at a rate of 0.1 Hz per channel. This implies an input data rate to the multiplexer of about 250 Bytes per sensor per second, or 1 KByte per second for all signals. Conversion of all channels may occur in approximately 1 second. Multiplexor circuitry 716 is also provided and will accept a 1 KHz data stream from all of the sensors of the array. Wireless transmission circuitry (e.g., Bluetooth and/or WiFi) 216 transmits to/from a local or remote processor.

While FIG. 7 depicts various connections between these units, this is schematic only and not limiting. The connections may be made by way of bus 720, or any other connection structure typical of such circuitry. The breakout unit 700 is coupled to the mattress sensor array, matrix, grid 722 (to be discussed below), and to a mattress display unit (MDU) 724 which may be co-located with the mattress or in the mattress itself as a stand-alone unit or as part of the breakout unit. The MDU 724 features the following, for each array sensor type (e.g., pressure, temperature, liquid, and/or acoustic): (i) Generation of a color map which displays a spatial distribution of the signals the entire sensor field, or a selected portion thereof. The user is able to alter the color scale to enhance intelligibility, and to zoom and pan over the map; (ii) Query the history of any sensor via a double click, which brings up the history of the sensor values over a user specified time interval, and (iii) Multiple correlation of any collection of sensor histories so as to detect possible common mechanisms for clinical disorder.

Figure 2:
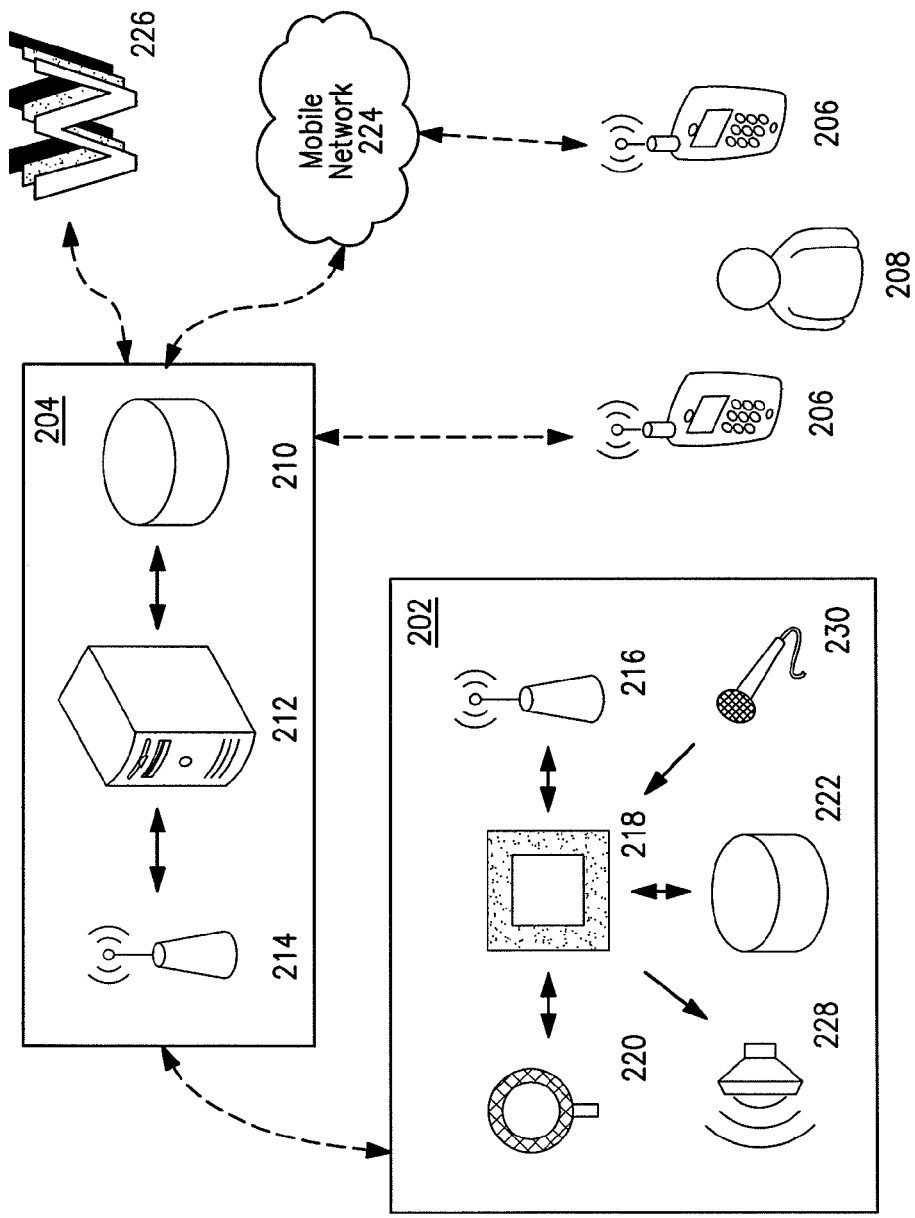
FIG. 2 is a diagram illustrating a first embodiment for using Smart Mattress.

Referring now to FIG. 2, the Smart Mattress system of FIG. 1 is shown in greater detail. The Smart Mattress 202 includes one or more sensors 220, which produce measurement data used in determining a patient's physiological state, such as patient vitals. Preferably, the sensors 220 include a sensor grid 772 (FIG. 7), and one or more patient-mounted sensors such as an ECG sensor system, EEG, an oximeter, pressure sensors, blood pressure device(s), piezoelectric elements, thermometers, insulin detectors, blood-oxygen sensor, impedance for plethysmography, carotid pulse wave detector(s), and/or any other physiological sensor capable of being interfaced with the breakout unit 700. In a particularly preferred embodiment, the sensor grid senses pressure and/or temperature and/or liquids, while an oximeter and/or ECG and/or blood pressure sensors are patient-mounted but coupled to the breakout unit 700 wirelessly or through cables plugged into the breakout unit connector panel (to be discussed below).

The processor 218 uses measurement data received from the one or more physiological sensors 220 and/or information stored to the internal memory (e.g., DSU) 222 to produce dynamic patient data. Dynamic patient data may include information such as a patient's physiological data, doctors' comments, and/or information useful to treatment of a patient, such as patient vitals (including, but not limited to, body temperature, Systolic and Diastolic blood pressure, ECG, SIDS, breathing rate, weight, oxygen saturation, acoustic pickup (e.g., detecting snoring—which may present a medical condition), and liquid-sensor). The DSU also stores patient identification data (or demographic data) such as name, height, weight, sex, date of birth, race, religion, blood type, treatment status and disposition, current patient history, provider name, date and time of last update, patient position, and triage information. The DSU also stores mattress data such as manufacturer, identification, location, maintenance, repair, and cleaning information. The stored data may be time-stamped and stored to the DSU 222 and/or wirelessly transmitted using transmitter 216. The Smart Mattress 202 may also include a microphone 230 and speaker 228 allowing for verbal communication between the Smart Mattress 202 user and portable device 206, monitoring station 110, and/or computer server 212. Preferably, the processor uses the dynamic patient data and/or the patient demographic data to generate one or more patient medical reports and/or records, which are stored in the DSU 222 and/or transmitted to the portable device 206, monitoring station 110, and/or computer server 212. The breakout unit is also capable of receiving data (wired and/or wireless). For example, modified patient medical records and/or mattress/bed data can be uploaded into DSU 222 for bedside access. Also, the portable device 206, the monitoring station 110, and/or the computer server 212 may transmit any command to the breakout unit, such a begin-scan command, an upload-medical-record command, a change-scan-timing command, a validate-sensor(s) command, and calibrate-sensor(s) command etc.

The DSU 222 is capable of collecting and disseminating patient information from initial patient assessment through disposition (to provide an electronic patient medical record), including triage, treatment and transport of patients for daily and mass casualty operations. To better prepare for disasters, major hurricanes, earthquakes, terrorist acts, mass casualty events and disease epidemics, the DSU 222 may link remote health care providers with on-scene responders and track patients from first assessment through triage, treatment, and transport. The DSU 222 may also store information regarding any medications and dosages (including intravenous fluids, morphine, and other medications), treatment status, disposition of treatment and physician comments/instructions/prescriptions, and include a time stamp of any update.

In a preferred embodiment, the Smart Mattress 202 uses Bluetooth® Technology to communicate patient and/or mattress data to/from a communication network 204 and/or to a monitoring station (e.g., a nurses' station). The communication network 204 includes a server 212, a wireless transmitter 214, and storage memory 210. The storage memory 210 may replicate the structure and functions of the DSU 222, and may store further data useful to medical care providers, insurers, governmental entities, etc. The communication network 204 is capable of receiving patient data from the Smart Mattress 202 via Bluetooth® technology or other wireless means (e.g., WiFi). The communication network 204 stores the received patient data in the storage memory 210 and/or wirelessly communicates it to a portable device 206, e.g., at a nurses' station or on a Doctor's PDA. The communication network 204 may use Bluetooth® technology to communicate with the portable device 206; however, depending on the required range, it may also use another method of wireless communication such as radio frequency communication, microwave communication, or infrared ("IR") short-range communication. The portable device 206 may be carried by a caregiver, nurse, and/or Doctor 208, or other personnel interested in the health of a patient. Conversely, any of the above data may be transmitted into the breakout unit from any of the portable unit(s)/nurse's station(s)/local server(s)/remote server(s). For example, when a new patient is transferred into the mattress/bed, the breakout unit can be commanded to erase the previous patient's medical record, and the new patient's medical record can be uploaded into the mattress.

In another embodiment, the communication network 204 is further capable of using a mobile network 224 (e.g. a cellular network, GSM, or other public communication channel) to communicate patient and/or mattress data to portable devices 206 capable of connecting to mobile network 224 including, but not limited to, a cell phone, smart phone or other hand held portable device. In certain embodiments, various existing portable device's 206 are modified merely by software and/or minor hardware changes to carry out patient monitoring/alarming. This capability is particularly useful in circumstances, for example, where the primary physician, or care giver, is on holiday or when the monitored patient is in home care. For example, a doctor attending a conference is Switzerland is able to quickly check the status of his US patients using only his smart phone and without interrupting the patient. Further, if any vital of a patient deviates from a predetermined range, the doctor, emergency medical personnel, and/or any medical staff may be instantly and automatically notified by an alarm, e-mail, call, page, message, or the like alert. This communication capability is also useful for validation and calibration of the sensors, which will be helpful for FDA approval and other quality/maintenance reporting requirements.

Similarly, patient and/or mattress data may also be pushed to the Word Wide Web 226 allowing a care giver 208 to access the information from any computer or PDA server by merely visiting a website and entering their identification information along with any other credentials useful in identifying the user. For security purposes, the website may further require the use of an authentication mechanism such as a piece of hardware (e.g. a token or USB) or software (e.g. a "soft token" for a PDA or cell phone) assigned to a computer user that generates an authentication code or password at fixed intervals. An exemplary authentication mechanism is available from RSA, the security division of EMC, at http://www.rsa.com.

Figure 3:
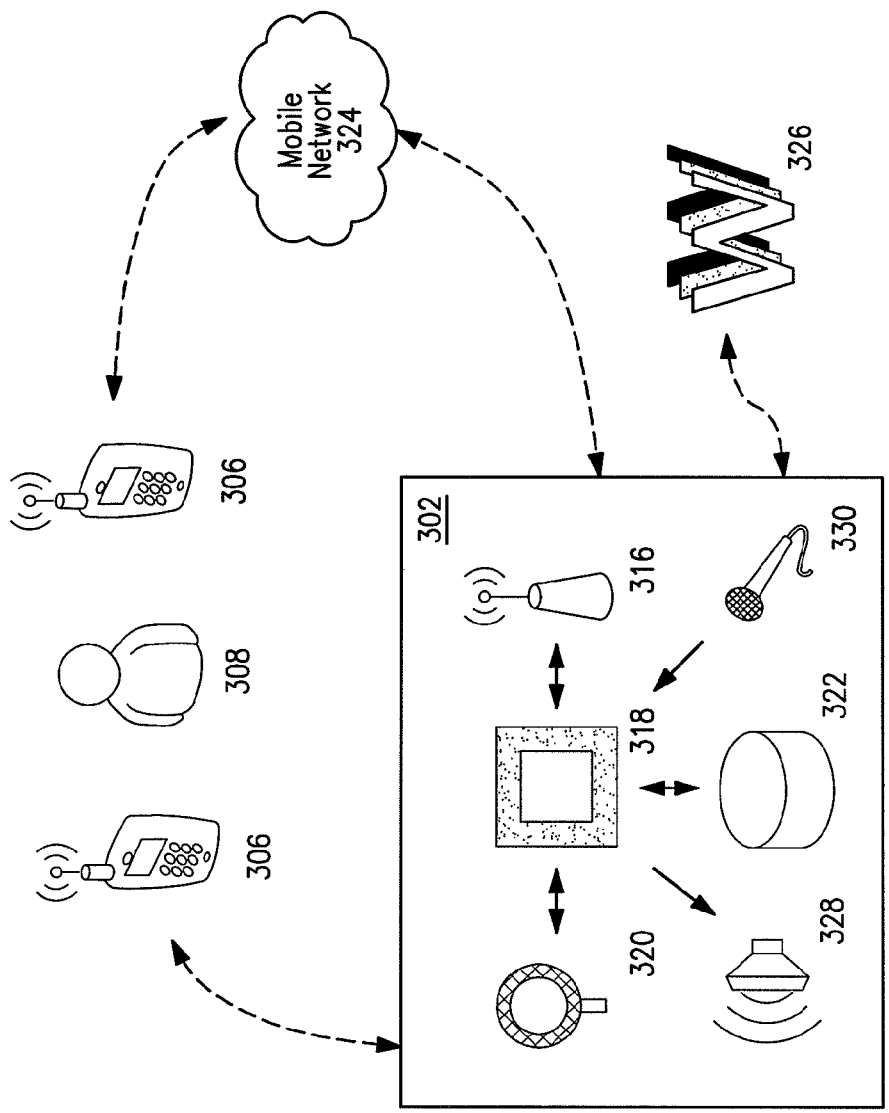
FIG. 3 is a diagram illustrating a second embodiment for using Smart Mattress.

Referring now to FIG. 3, another embodiment of the present invention is shown. As in the prior embodiment, the Smart Mattress 302 includes one or more sensors 320, which produce physiological measurement data used in determining a patient's physiological state, like those discussed above. The processor 318 uses measurement data received from the one or more sensors 320 and information is stored to the DSU 322 to produce patient data. As distinct from the prior embodiment, in this embodiment, the Smart Mattress 302 may use Bluetooth® Technology to communicate patient and/or mattress data directly to a portable device 306. Preferably, the portable device 306 may be carried by a caregiver 308 or other personnel interested in the health of a patient. Alternatively, the Smart Mattress 302 may be capable of pushing the dynamic patient data to the World Wide Web 326 or to a mobile network 324 which may transmit the dynamic patient data to one or more portable devices 306.

To eliminate the need for multiple devices, a single portable device 306 may include all of the hardware and/or software necessary to make the portable device capable of communicating with the Smart Mattress 302 in any of the ways describes above.

Figure 4:
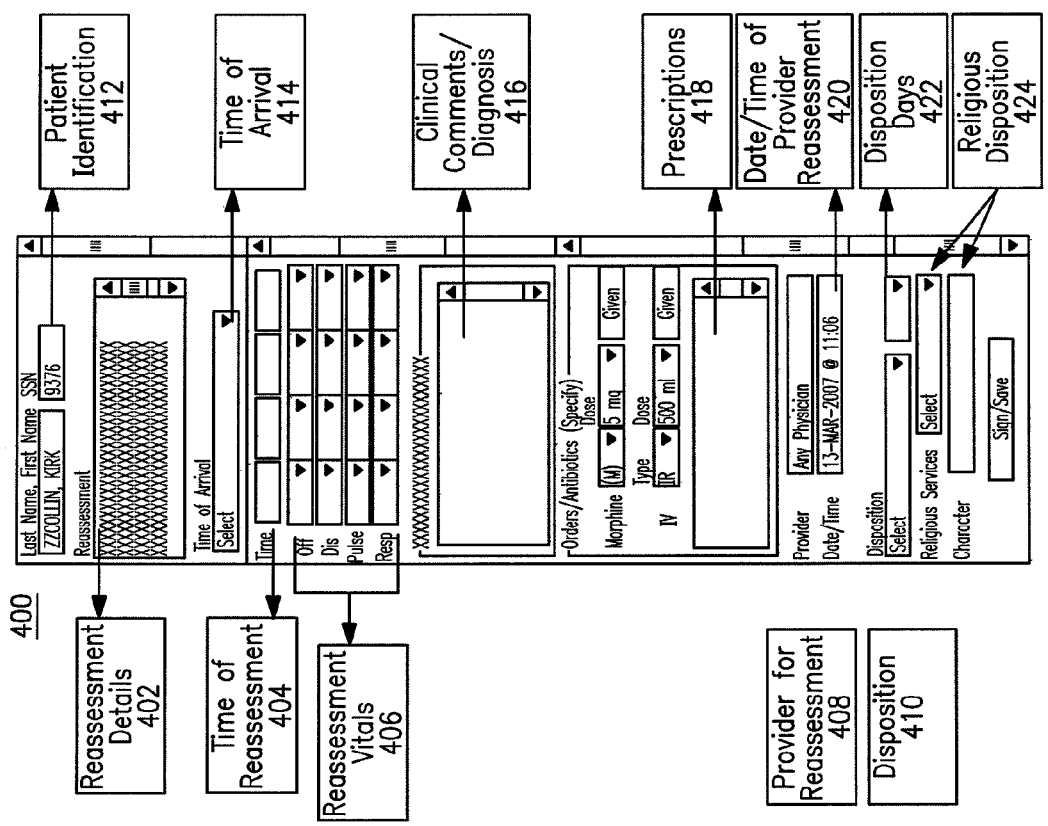
FIG. 4 is an exemplary screen shot of the portable device.

FIG. 4 is an exemplary screen shot of the display panel of the portable devices disclosed in FIGS. 1, 2 and 3. In FIG. 4, the portable device 400 is capable of displaying a number of patient vitals as well as other patient and/or mattress data either simultaneously or within a plurality of windows. The portable device 400 contains patient details 412 such as a patient's name, time of arrival 414, social security number, hospital identification number, medications, allergies, prescriptions, etc. The portable device is also capable of displaying reassessment vitals 406 (e.g., physiological data) which are measured via a Smart Mattress. In addition to reassessment vitals, the time of reassessment 404 and details of the reassessment 402 may be displayed. These fields would include information regarding any changes to the patient's status and some background on the patient's health, as well as the time of the most recent reassessment and of prior assessments. The portable device 400 also stores information regarding the health care provider and/or physician responsible or on call for the patient. A provider for reassessment 408 is displayed along with the time of the most recent or next reassessment 420. Other useful fields are the clinical comments and diagnosis field 416 and prescriptions 418 or current drug/IV rations. The portable device 400 may even provide miscellaneous information such as a patient's religious preference 424, current disposition 410, and the duration of a patient's disposition 422. Naturally, the portable device would include an interactive means (e.g., a keyboard, touch screen, and/or voice command) to allow a physician or caregiver to input new patient data or comments or to change existing patient data or comments. Any additions or changes to a patient's profile would be communicated to the Smart Mattress DSU, as well as to any intermediate computer servers, so that data stored on the mattress, the portable device and the computer server is constantly synchronized.

In certain embodiments, the portable device 400 may also provide voice communication functionality which allows for real time communication between the patient and the care giver. This may be accomplished using over-the-air radio, short wave, cellular, GSM, internet or other communication methods known in the art, to/from a microphone/speaker apparatus mounted on the mattress and/or the patient. If the patient or caregiver is unavailable, the portable device 400 and/or Smart Mattress may also be capable of recording voice messages, communicating recorded messages, and/or storing/accessing recorded messages from a network (e.g. voicemail).

Figure 5:
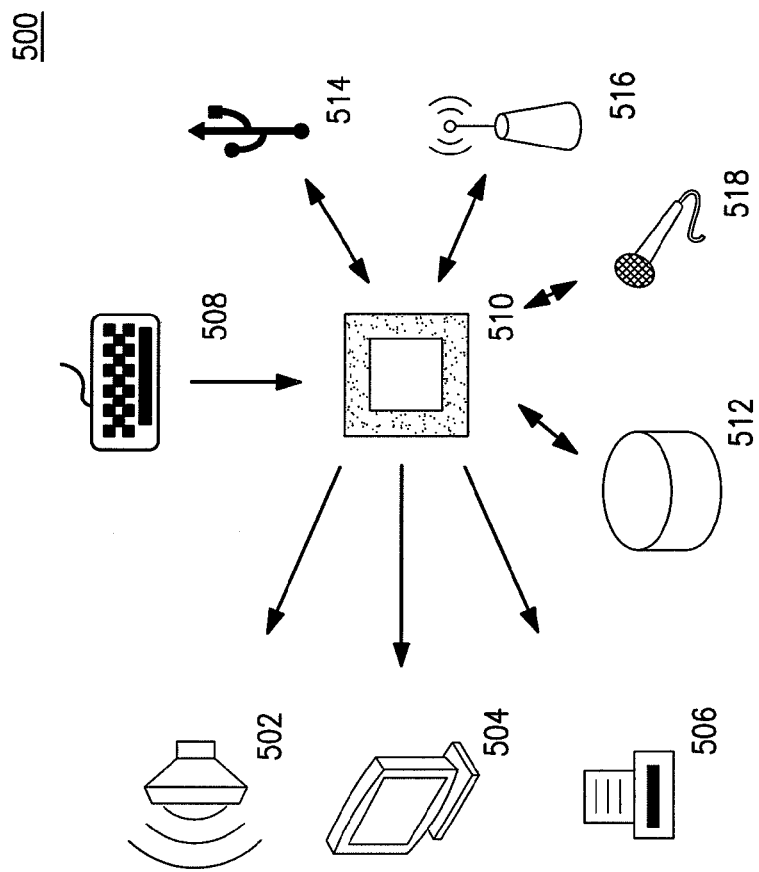
FIG. 5 is a diagram illustrating a portable device.

Referring now to FIG. 5, the portable device 500, processor 510, DSU 512 and wireless transmitter 516 are shown. As with the Smart Mattress, the portable device 500 includes a processor 510 and may use Bluetooth® technology or other wireless means to communicate with other devices, including a Smart Mattress, computer network, or other devices. Data may be modified or inserted using a manual user interface 508, such as a keyboard, touch screen, and/or voice command. Patient and/or mattress data, software, and any other data or programs may be stored in the DSU 512. The DSU 512 may be removable or internal. In certain embodiments, the DSU 512 may include both an internal memory and removable memory (e.g., flash memory) to allow for easy data transfer and backup. The portable device 500 may also include a wired communication port 514 such as USB or FireWire. The wired communication port 514 allows for connection to and communication with other devices such as a computer. The portable device 500 also includes one or more audio-visual components, such as a screen 504 (e.g., LCD display), one or more speakers 502 and, in certain embodiments, a portable printer 506. The portable printer 506 could be used to print patient medical reports or medical prescriptions on the spot, eliminating the risk of an error in reading an illegible doctor's note or prescription. The printer may integrated into the portable device or connected by wired or wireless means (e.g. Bluetooth).

Figure 8:
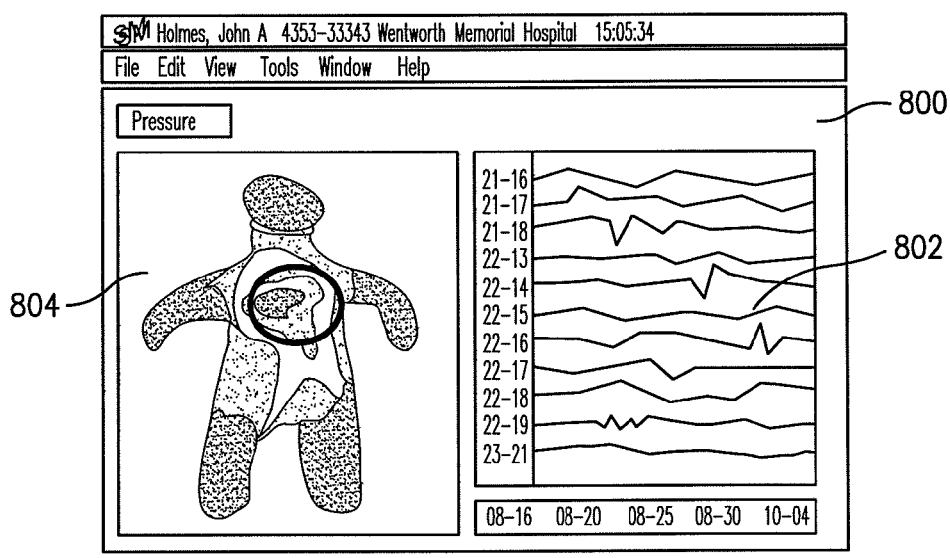
FIG. 8 shows an example of a patient display presented on the display of a mobile unit.

FIG. 8 shows an example of a patient display 800 presented on the display 504 of the mobile unit 500. For example, where the Smart Mattress includes a grid of sensors detecting pressure (to be described below), the pressure output of numbered sensors 21-16 through 21-21 may be shown in graph form 802. A color-coded representation of the patient's body may be displayed at 804, with the darker areas showing areas of lighter pressure. This will be instrumental in displaying, diagnosing, and treating decubitus ulcers.

Figure 6:
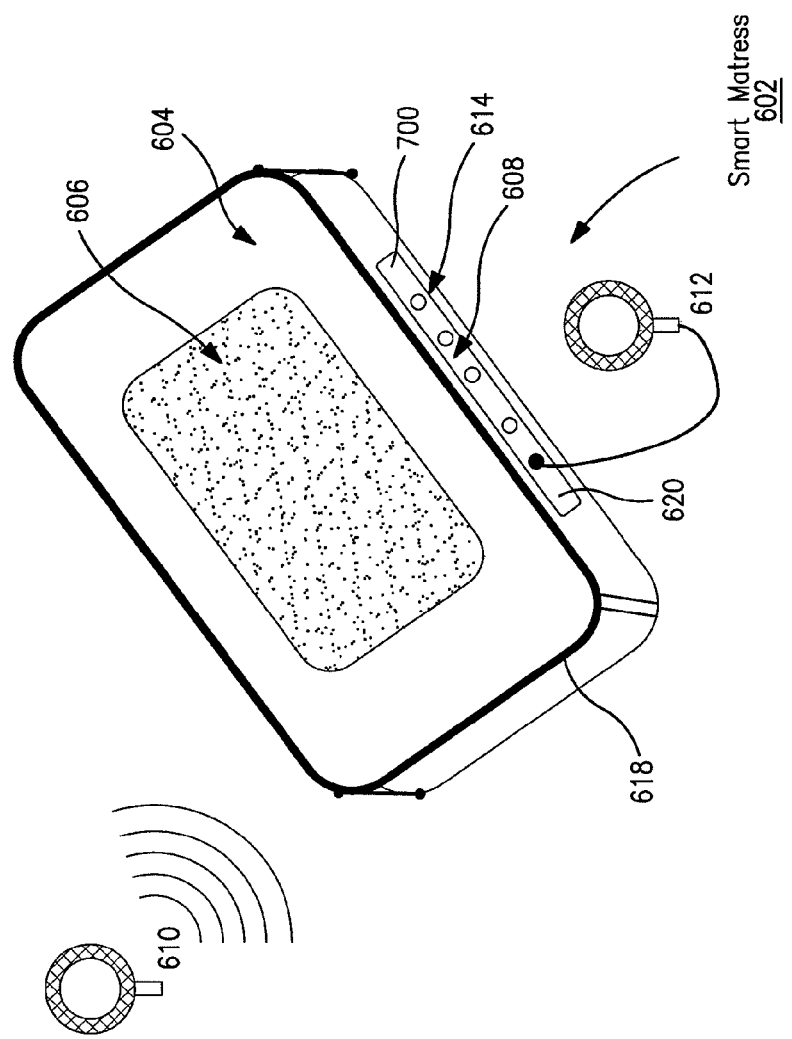
FIG. 6 is a diagram illustrating an exterior embodiment of a Smart Mattress.

Referring now to FIG. 6, an example diagram of an uncovered Smart Mattress 602 is shown. A Smart Mattress 602 should be capable of providing all of the disclosed monitoring features while still providing the comfort and safety features usually associated with traditional and/or hospital mattresses. The mattress 602 may be constructed from a number of materials (e.g. traditional inner spring, foam, air, gel, water, etc.). The mattress 602 may also have a firmer (and/or higher) perimeter 604 to help keep the patient centered on the mattress and in substantially constant contact with one or more sensor pads 606. Additionally, the underside of the mattress 602 may have fasteners, such as magnets, and/or hooks and loops (e.g. VELCRO), to help keep bed linens in place and to keep the mattress 602 from sliding or shifting.

The mattress top surface may include one or more sensor pads 606, or sensor areas, capable of detecting and/or measuring a patient's physiological characteristics from under a sheet and without sacrificing comfort. A single sensor pad 606 is depicted; however, a number of sensor pads 606 in various shapes, sizes, and sensitivity levels may be used. The one or more sensor pads 606 may be completely integrated with the mattress 604 or detachable to allow easy replacement if damaged. In the preferred embodiment, the sensor pad 606 is disposed within the mattress, under the top mattress surface or top upholstery layer (e.g., the comfort layer, typically comprising an insulator, a middle upholstery layer, a quilt layer, and the ticking), although the sensor pad(s) may be installed in between any of the top upholstery layer. Preferably, the sensor pad is installed in a protective envelope (to be discussed below). The sensor pad(s) 606 may be hard-wired to the breakout unit 700 or may utilize a detachable plug or clip. In either variation, it would be advantageous to connect each sensor pad 606 to the breakout unit 700 such that any sensor cables are not visible. The cable(s) may sit in one or more trenches or grooves in the mattress surface. Alternatively, the mattress sensor pad(s) 606 may be installed in a traditional mattress pad, or in an envelope 618 which may be coupled to the top surface (and perhaps to one, two, three, or four of the side surfaces as well) of the mattress. In any event, the material covering the sensor pad(s) 606 should be water and stain resistant, breathable, and waterproof, such as the material now used for hospital scrubs. Some water permeability, however, may be desired so that the sensor pad(s) 606 may detect the presence of liquids such as urine and/or blood.

When a patient lies on the Smart Mattress 602, the one or more sensor pads 606 gather physiological characteristic data in real time. The one or more sensor pads 606 may gather data including, but not limited to, pressure, temperature, blood pressure, blood-oxygen, weight, breathing rate, heart rate, sound, liquids, etc. Weight may detected by summing (integrating) the outputs of one or more of the pressure sensors of the sensor pad, and then calibrating the outputs for various weights. Alternatively, weight could be measured by placing a sensor pad beneath the mattress and then determining the distances between the sensor pad 606 elements and the bottom sensor pad element(s); weight will vary as a function of such distances.

An exemplary sensor pad is the Non-Invasive Analysis of Physiological Signals (NAPS) system that was designed and developed at the Medical Automation Research Center at the University of Virginia. The NAPS system pad uses ballistocardiography (BCG) to detect minute forces generated during cardiac contraction and relaxation, and can also detect body movement from respiratory effort and postural changes. The system disclosed in U.S. Patent Publication No. 2005/0124864 to Mack, which is hereby incorporated by reference in its entirety herein, discloses a system for non-invasively detecting, monitoring, and analyzing physiological characteristics using a mattress pad. The system relies on a highly sensitive pressure transducer pneumatically connected to a compliant force-coupling pad installed on a mattress.

In certain embodiments, all of a patient's physiological characteristics might not be easily monitored using a sensor pad 606. In this situation, one or more wireless sensors 610 may be equipped with Bluetooth technology allowing the wireless sensors 610 to communicate directly with the Smart Mattress 602. In addition to (or alternatively) wired sensors 612 may be used. Such wireless and/or wired sensors may include ECG, oximeter, thermometer, heart rate, blood pressure, and/or breathing rate sensors, etc. In the case where wired sensors are used, the breakout unit 700 may have a connector panel 620, which may include one or more terminals 608 with a number of wired connectors 614 that allow for the connection of one or more traditional wired sensors 612. Depending on the application, each terminal 608 may contain a single connector type or, to enhance flexibility, a variety of connector types such as RS-232, Ethernet, US-B, RCA, coaxial, etc. The terminals 608 may be located on one or more of the sides of the mattress 604, however, for convenience, it may be advantageous to install the terminals 608 on a mattress 604 side and closer to the head end and adjacent to or affixed to the breakout unit 700.

Figure 9:
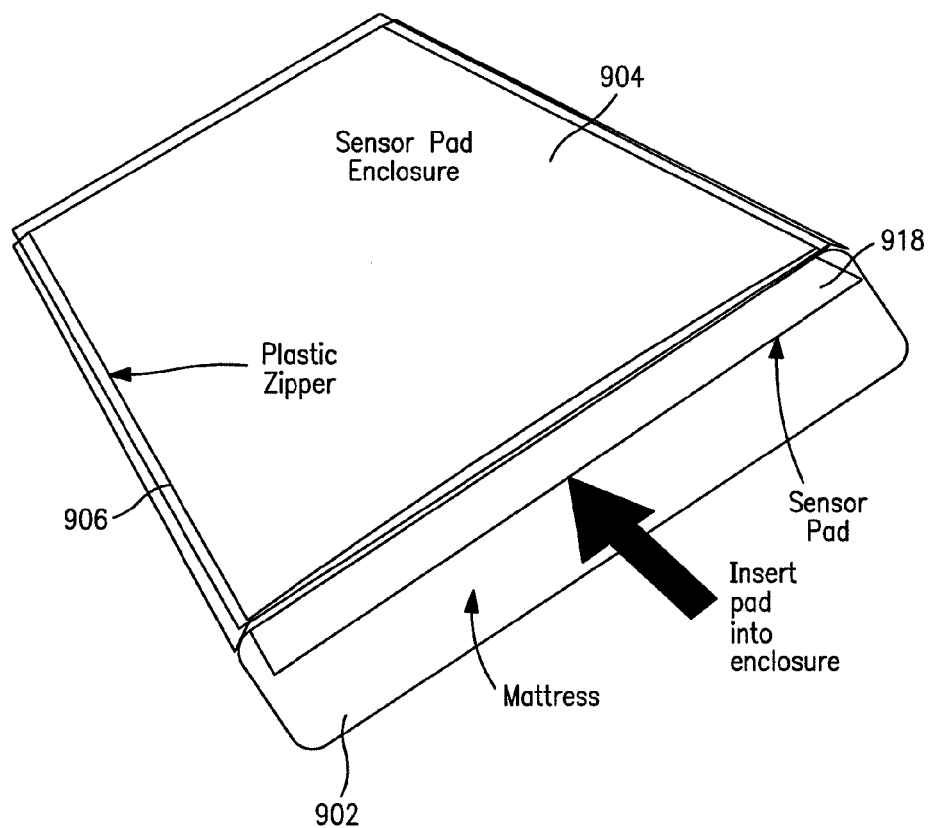
FIG. 9 is a schematic perspective view showing a preferred embodiment of the Smart Mattress with the sensor pad(s) installed in an envelope enclosure affixed to the top surface of a mattress.

FIG. 9 is a schematic perspective view showing an alternative embodiment of the Smart Mattress, with the sensor pad(s) installed in an envelope or enclosure 904 affixed to the top surface of a mattress. This embodiment is useful, for example, in retro-fitting a current mattress with the Smart Mattress technology. As one example, the envelope 904 may comprise a fabric with water-shedding properties and defibrillation protection. For example, Mertex-Plus fabric is a 3-layer impervious, reusable, micro fiber possessing excellent repellent and/or absorbent properties, suitable for use in potentially contagious procedures where 100% protection is required. It contains carbon yarn which provides defibrillation protection to the sensor pad sensors and wiring. In FIG. 9, a standard foam mattress 902 has the sensor pad enclosure 904 affixed to the top surface thereof by, e.g., straps, Velcro, zippers, magnets, etc. One, two, three, or four sides of the sensor pad enclosure 904 preferably has/have a plastic zipper closure 906 for access to the inside of the enclosure. The sensor pad(s) 918 can be inserted into the enclosure 904 through one or more of the zipper openings. Preferably, the sensor pad enclosure 904 is designed for patient comfort. The sensor pad enclosure 904 should also provide a uniform pressure transfer function, and not interfere with the accuracy of the sensor readings. The sensor pad enclosure 904 should be easily removable for cleaning, sanitation, and repair, and also may be impervious or semi-impervious to body fluids. The entire enclosure, both top and bottom, should not admit (under long term usage) transmission of fluids such as blood and urine to the electronic components of the pad, unless liquids are to be detected.

Figure 10:
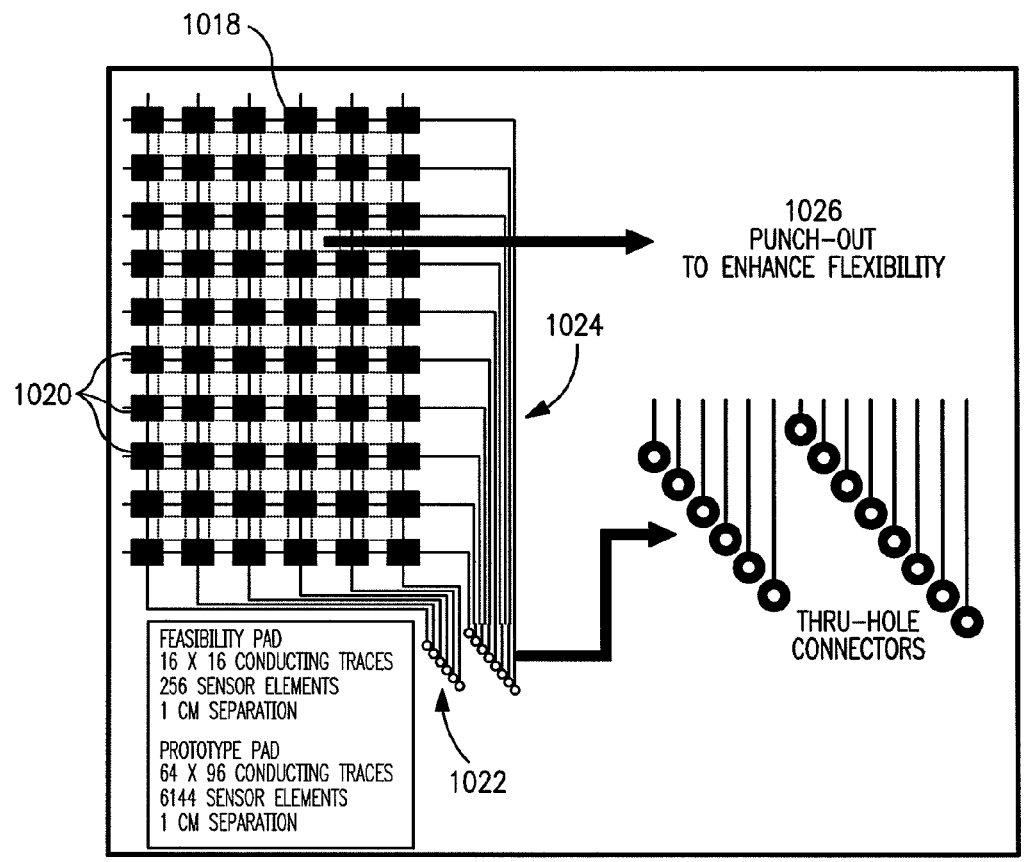
FIG. 10 is a schematic of the sensor pad wiring arrangement.

FIG. 10 is a schematic of a preferred sensor pad showing the sensor pad wiring arrangement (only a portion of the wiring is shown, for clarity). A sensor pad 1018 includes a plurality of sensors 1020 coupled to a sensor mesh comprising a plurality of column conductors 1022 and a plurality of row conductors 1024. A first prototype of the preferred sensor pad was constructed having 256 sensor elements at a 1 cm separation. A full-scale pad may comprise, e.g., 6144 sensor elements coupled by 64 column conductors and 96 row conductors. Preferably, the sensor pad substrates are polyethylene, although printable microfibers or other textiles and/or fabrics could be used. The conductors are a first type of conductive ink printed on the substrates, while the sensor elements comprise a second type of conductive ink, one sensitive to pressure and/or temperature and/or liquid. For example, Creative Materials, Inc. of Boston, Mass. produces acceptable inks and adhesives for this application. In particular, the conductors may be screen-printed silver compounds, while the sensors may be screen-printed carbon compounds. Preferably, the end of each conductor terminates in a circular through-hole to simplify coupling to the connector (to be discussed below). It has been found that the flexibility of the pad can be enhanced, and the electrical conduction greatly improved by punching one or more square or circular holes 1026 through the pad in-between the sensors and the conductors, as shown. Without the holes 1026, when a person lies on the pad, the folds and wrinkles therein may cause varying resistance in the conductors, leading to poor signal stabilization and poor signal-to-noise ratio. The holes allow the pad to remain relatively flat, improving signal detection, stability, and accuracy in the conductors. A liquid sensor may comprise one or more conductors without coupled sensor elements. The presence of liquid is sensed by electric and/or magnetic field changes surrounding the conductor(s).

Thus, the pad 1018 comprises an array of sensors embedded in a flexible material pad which covers a mattress and which reports the spatial distribution of pressures and/or temperatures generated by a person lying on the pad. The pad is preferably sampled at a user-selected frequency and the sensor values are assembled at the breakout unit processor attached to the pad. In turn, the breakout unit transmits by wire and/or wirelessly to the MDU 724, which may be local or at a remote location. At the MDU 724, the sensor values are preferably plotted in real time as a color coded body map 804 (FIG. 8). This map may be used to compute and track important vitals such as respiration and the formation of decubitus ulcers.

Figure 11:
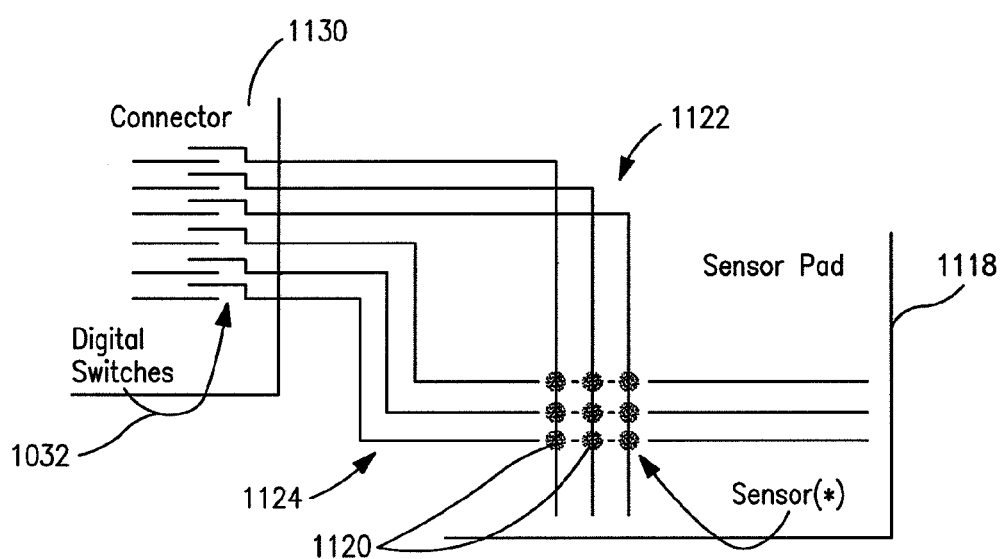
FIG. 11 is a partial schematic showing some of the pad sensors, some of the pad conductors, and how they are coupled to the connector.

FIG. 11 is a partial schematic showing some of the pad sensors, some of the pad conductors, and how they are coupled to the breakout unit. The sensor pad 1118 has sensors 1120 coupled to the connector 1130 through column conductors 1122 and row conductors 1120. Digital switches 1032 in the breakout unit 700 can be opened and closed under processor-control in order to scan the signals coming from the sensors. The sensor pad can be interfaced with the processor 218 through any known connector terminal, or wirelessly. The breakout unit 700 is preferably powered by rechargeable, replaceable batteries. The time to fully charge is preferably less than 6 hours. The battery life, under normal conditions is preferably greater than 1000 hours. As an example of a wired connector for a smaller pad covering half the mattress, the connector preferably accommodates at least 32 rows by 32 columns (1024 sensels per pad). The breakout unit 700 is preferably able to acquire 10 pad frames per second @2 Bytes per sensel; thus providing for a sampling rate of approximately 20 Kbyte/sec. The breakout unit 700 preferably outputs a serial USB data stream to the MDU and/or remote unit. Further, the breakout unit 700 accepts commands, encoded as the output stream, from the MDU and/or remote unit. The breakout unit 700 preferably supports both Bluetooth communication in the case that the MDU is situated locally, and WiFi in the case that the MDU is to be found at a remote IP address. In the case where the MDU is remote, communication over the Internet is preferably be expedited via a third party server.

Figure 12A:
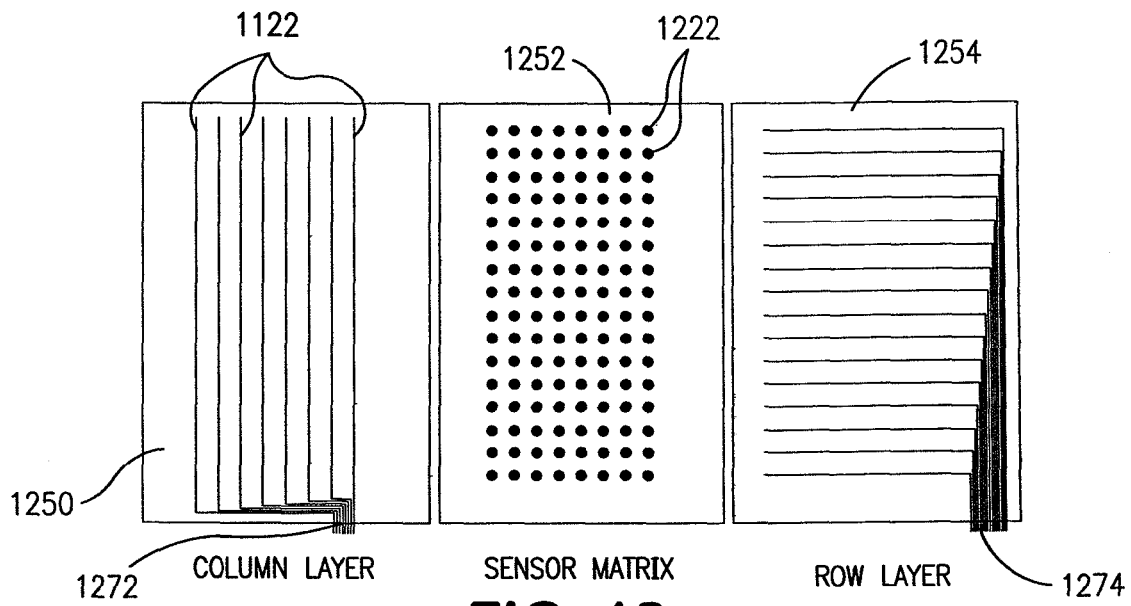
FIGS. 12a, 12b, and 12c are notional schematic drawings showing the assembly of the sensor pad.
Figure 12B:
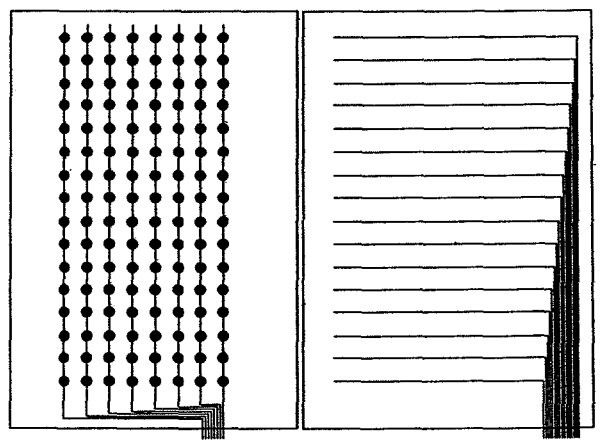
Figure 12C:
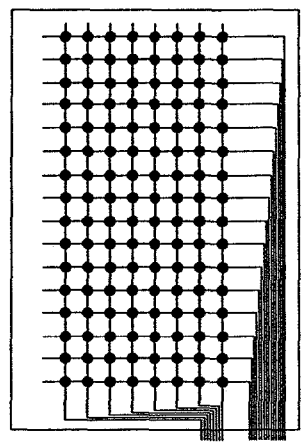

FIGS. 12a, 12b, and 12c are notional schematic drawings showing the assembly of the sensor pad. In FIG. 12a, the column layer 1250 comprises a series of parallel column conductors 1122 embedded and/or printed and/or adhered to one side of a substrate, such as a 5 mil sheet of polyethylene plastic. This layer is proximal the mattress. The sensor layer 1252 comprises a series of pressure and/or temperature and/or liquid sensing elements 1222; preferably, those whose electrical resistance varies as a function of pressure and/or temperature and/or liquid. For example, when sensing pressure, each sensing element has an electrical resistance density which is a calibrated nonlinear function of pressure across the layer. The sensing elements 1222 are embedded as a series of dots, squares, triangles, and/or other shapes on a polyethylene sheet. The row layer 1254 comprises a series of row conductors 1224 embedded on a polyethylene sheet. As shown in FIGS. 12b and 12c, the sensor layer 1252 is placed atop the column layer, and the row layer is placed atop the sensor layer 1252. The three layers are fixed together by heat treatment and/or adhesives. If desired, additional sensor layers and conductive layers can be sandwiched together such that each sensor layer detects one parameter. For example, a first sensor layer may detect pressure, a second sensor layer may detect temperature, and a third sensor layer may detect liquids. Of course, as many sensor layers may be added as desired, but it would be preferable to combine as many sensing functions into as few layer as possible. Preferably, the top and bottom layers are made from a flexible, nonconductive material, such as low durometer neoprene rubber. Optionally an additional layer may be added on top to suit the comfort of the patient. Each printed conductor connects to an insulated conductor 1272, 1274, which runs along an edge or off the edge of the pad. These conductors are terminated by means of a digital switch located on the PCB connector 1130 as illustrated in FIG. 11. For example, to measure the pressure at the intersection of a given row and column, the column switch is closed and a voltage applied to the column through the connector. The corresponding row switch is closed and the output voltage measured by the connector. The scanned voltage measurements are synthesized into a whole-body matrix, for example, the color graph of FIG. 8.

In a particularly preferred embodiment, non-pressure-sensitive, conductive-ink row conductors are first printed on a 5 mil polyethylene sheet. An adhesive is then applied at every spot where a pressure-sensitive conductive ink sensor is to be applied. One half of the pressure-sensitive conductive ink which comprises each sensor is then applied over the adhesive. This process is then mirrored for the column conductors. The two sheets are then pressed together and heat treated to seal the pad.

An alternative embodiment features the sensing elements 1222 detecting movement of the patient through detection of shear forces on each sensor element 1222. Specifically, in the case of pressure, each sensor element detects compaction of the conductive ink. Conductive inks are now available which detect stretching of the ink by a change of resistance in accordance with stretching. With such inks, shear stresses can be measured and calibrated in accordance with patient movement. This will help in detection and treatment of decubitus ulcers. As another means of detecting movement, a body-scan of pressure sensors may be stored in memory, and then compared with future scans taken at predetermined intervals. In a further alternative, pressure-sensing and shear-sensing sensors are interweaved on the same sensor pad; even sensors detect pressure, while odd sensors detect shear. This embodiment may be expanded to interweaving sensors, such as pressure, temperature, liquid, shear, etc., in any combination and in any pattern.

Preferably, the leakage current to which a patient is exposed does not exceed 5 mA in the case of a sensor pad with the maximum number of rows and columns. Defibrillation protection is provided by the connector being designed and tested such that it does not fail when a 5 KV pulse is applied between any input leads for a period of 10 seconds. This pulse represents the maximum shock delivered when a patient is defibrillated while on the pad. The Connector is preferably isolated from the patient, and all RF communication is preferably effected with commercially available transceivers which have met the FCC requirements for EMI. Defibrillation protection is provided by the Mertex-plus envelope and/or by electrical isolators installed on the pad or in the breakout unit.

Figure 13:
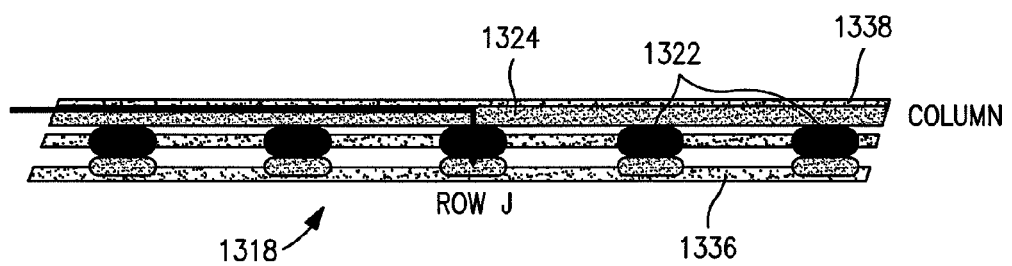
FIG. 13 is a notional cross-sectional view of the pad showing the sensing elements, the column (or row) conductors, and the row (or column) conductors.

FIG. 13 is a notional cross-sectional view of the pad 1318, showing sensing elements 1320, column (or row) conductor 1322, and row (or column) conductors 1324. The bottom substrate is 1336 and the top substrate is 1338. These substrates are supportive, non-conducting material such as polyethylene, rubber, fabric, and/or neoprene. The conductive traces may be woven into the supportive material, and extend preferably beyond the material on one side for connection. This could be accomplished by the bi-laminar row-column construction. Alternatively, as described above, the conductive trace could be printed with conductive ink on the supportive non-conducting material. The column to which the input voltage is supplied is selected by closing the I-th column switch in the electronic connector, while the row through which the output voltage flows is selected by closing the J-th Row switch in the connector, under control for the breakout unit and/or MDU. The circuit is preferably a simple series of resistors from which it follows that $$V_{out}=V_{in}-I[R_{col\,I}+R_{row\,J}+\rho(p_{IJ})] \quad (1)$$

and therefore the pressure at Column I, Row J is calculated as $$p_{IJ}=\rho^{-1}(V_{out}-V_{in}+I[R_{col\,I}+R_{row\,J}]). \quad (2)$$

2. Functions

The breakout unit 700 described above includes the mattress sensor grid, the DSU for storing (i) patient vitals (including, but not limited to, body temperature, (perhaps Systolic and Diastolic blood pressure), ECG, SIDS, breathing rate, weight, oxygen saturation, acoustic, and liquid-presence), (ii) other patient information (including, but not limited to, name, height, weight, sex, date of birth, race, religion, blood type, treatment status and disposition, current patient history, provider name, date and time of last update, patient position, and triage information), and (iii) mattress information (including, but not limited to, manufacturer, identification, location, maintenance, repair, and cleaning information) The breakout unit also includes a processor 218 for handling, processing and/or time-stamping any updates to a DSU. The sensors may be embedded in the mattress and/or directly coupled to the patient. When the sensor is coupled to a patient, the Smart Mattress may wirelessly communicate information with the sensor using short-range wireless communication, e.g., Bluetooth technology. Alternatively, the Smart Mattress may include ports where additional wired sensors may be connected by the user. As another alternative, the breakout unit itself may comprise the MDU, with a display, keyboard, and/or touch-screen GUI.

The Smart Mattress includes an on-board power source, such as a rechargeable battery, to increase the portability of a Smart Mattress. The rechargeable battery may be recharged using the standard AC wall current, or the battery may be removed and charged using a dock or charging station. Alternatively, a Smart Mattress may be capable of receiving power directly from an auxiliary power source (e.g., wall socket, solar panel or other generator).

The DSU is capable of collecting and disseminating patient information from initial patient assessment through disposition (to provide an electronic medical record), including triage, treatment and transport of patients for daily and mass casualty operations. To better prepare for disasters, major hurricanes, earthquakes, terrorist acts, mass casualty events and disease epidemics, the DSU may link health providers with on-scene responders and track patients from first assessment through triage, treatment and transport. The DSU may also store information regarding any medications and dosages (including intravenous fluids, morphine and other medications), treatment status, disposition of treatment and physician and include a time stamp of the last update.

Sensors or other monitoring devices should be in constant proximate contact with a patient, allowing for continuous updates to the data in a mattress's DSU. The Smart Mattress may also be capable of simultaneously updating a medical facility's information system and a provider's or first responder's portable device with a patient's vital sign information. Simultaneously updating a medical facility's information provides a backup in the event of data loss in the Smart Mattress.

Updates regarding a patient's information may be communicated using wireless technology between a medical facility, health care provider or portable device and the DSU in the Smart Mattress. Similarly, if patient information (e.g., vitals or health condition) deviates from an established range or value, that information may also be wirelessly communicated to a health care provider either directly from a Smart Mattress or via a computer network.

Two of the more popular types of wireless technology standards available are Bluetooth® and the Institute of Electrical and Electronic Engineering's (IEEE) 802.11 standards ("Wi-Fi"). Bluetooth® is an open specification delivering short-range radio communication between electrical devices that are equipped with Bluetooth® chips. When two Bluetooth®-enabled devices are within communication range (presently about 10 meters), they send each other a unique ID to identify one another. This ID is used to determine the type of information to be shared and the level of functionality that could occur between the two devices. However, Bluetooth® is not designed for long-distance communication but rather as a means for providing connections between mobile computing devices or between a mobile computer device and a hub. To increase operating range, an potential solution would be to couple Bluetooth® technology with Wi-Fi, which has a larger operating range of up to 300 meters. Wi-Fi is an extension of the wired Ethernet and uses the same principles as its wired counterpart, thus providing its users with high-speed, reliable connections to a network. Alternatively, a Bluetooth® range extender may be integrated into the system to enhance the communication range and to eliminate the need for Wi-Fi.

A medical provider may utilize the portable device to access and update patient information stored in a Smart Mattress. Using the portable device allows for more flexibility when monitoring a patient or during emergency evacuations by allowing the health care provider to monitor from a distance or to receive automatic alerts when a patient's condition changes. Since patient vitals and demographic information are stored in the Smart Mattress's DSU, there is no need to input this information when updating a patient's status and disposition during relocation or evacuation. The Smart Mattress DSU also eliminates the need for a paper-based system both during emergency evacuations and in general patient monitoring. Medical staff or health care providers are able to conduct a reassessment of a patient's condition and upload those comments to the DSU in a mattress using a portable device. The time of a reassessment may also be automatically time-stamped in order to track a patient's condition. A provider will additionally be able to note what time a patient arrived at a certain location.

The portable device allows a care provider to review patient information from a distant location, make a diagnosis and upload that information to a DSU in a Smart Mattress via wireless or wired communication. Additionally, if a health care provider feels a patient needs immediate medical care, the provider may order certain actions that would be sent to on-site personnel, a medical unit or an evacuation site. Provider-directed actions could also be sent directly to a staff member's portable device. Ideally, the hospital or evacuation site would have a monitoring station that is capable of communicating information with a Smart Mattress, similar to an intensive care unit's nursing station which monitors patient information, enabling quick medical decisions.

The Smart Mattress is ideal for use as an emergency evacuation mattress for bed-ridden patients. This is due in part to a Smart Mattress being self-contained, capable of monitoring vital statistics of a patient in real time, analyzing data using an embedded processor, storing patient identification and information, producing an electronic medical report, and communicating any data to the caregiver or computer server using wireless technology. Integrating Smart Mattress functionality (e.g., the features of a Smart Mattress) with an evacuation mattress, such as the Evacusled, is a life-saving combination.

An Evacusled, or evacuation mattress, is disclosed in U.S. Patent Publication No. 2008/0301876 to Christopher Kenalty, and is hereby incorporated by reference in its entirety herein. Evacusled teaches an emergency evacuation mattress for bed-ridden patients that is capable of operation by a single caregiver, provides a warm and secure cocoon for a patient, allows easy transport over any type of surface, provides proper support for all of a patient's body and bedding, and allows a patient to feel a high degree of comfort in what is otherwise a very stressful situation. The Evacusled would be an ideal candidate for integration with the Smart Mattress and/or Smart Mattress functionality.

Several other advantageous evacuation devices and techniques are also disclosed in U.S. Pat. No. 5,249,321 to Jorg Graf and U.S. patent Ser. No. 12/700,027, filed Feb. 4, 2010, to Christopher Kenalty, which are incorporated by reference herein.

The Smart Mattress is also ideal for detecting symptoms of SIDS. The sensor pad array of pressure-sensitive elements is capable of detecting both respiration (breathing rate) and heart rate. Signal processing will filter, normalize, and amplify the detected pressure signals to determine the pressure variations caused by breathing and heart-beats. One or both of these signals can be compared to predetermined thresholds (which may be set or modified by the user or medical staff) to detect abnormal breathing or cardiac arrhythmia. For example, if regular breathing stops for 7 seconds, and/or a regular heart-beat stops for 5 seconds, an alarm signal will be generated. The alarm signal can be a local audible signal to stimulate the patient, and/or transmitted wirelessly to a parent or care-giver.

Another area of concern during patient evacuation is accurate tracking of a patient and mattress. This may be solved by utilizing Radio-Frequency Identification (or "RFID") tags and/or GPS transceivers embedded inside the Smart Mattress, enabling real-time location and movement information which can be sent to remote monitoring equipment or medical staff during emergency evacuation—ensuring a facility has not left anyone behind.

The Smart Mattress, either alone or in combination with the Evacusled, should be capable of providing all of these novel features while still providing the comfort and safety features usually associated with traditional and hospital mattresses. For example, the Smart Mattress should be designed to reduce the potential for pressure ulcers. This can be accomplished using embedded sensors in the mattress that would map pressure points and alert medical staff when an area exceeds the established threshold. All pressure point information may also be stored in an embedded DSU.

The Smart Mattress may include a cover (e.g., nylon, vinyl, plastic) to help reduce the likelihood of fluid penetration and prevent damage to electronic devices stored in the mattress. Having a firmer perimeter foam built into a Smart Mattress could help keep a patient centered on the mattress at all times and therefore reduce the risk of rolling out of bed. The Smart Mattress and Evacusled components will be radiolucent to allow x-rays to pass through them. A critical care bed should have a radiolucent platform attached to the bed deck and a radiolucent mattress, or Smart Mattress, to allow the use of fluoroscopy at the bedside. To allow for bedside x-ray use, the Smart Mattress and Evacusled combo should both be radiolucent, a feature that, due to its versatility and ease of use, will be well-received in the critical care bed market.

A potential alternative to creating a 100% radiolucent Smart Mattress and Evacusled combo is to create an x-ray cassette sleeve in the side of the mattress. The side opening allows for easy insertion of an x-ray cassette. The sleeve could be located under the top of the mattress (e.g., approximately 1 inch deep) so as not to be in direct contact with the patient. This method would increase patient and caregiver safety and reduce the chances of injury associated with portable x-ray procedures.

During daily use, the external skin of the Smart Mattress may become dirty, damaged or torn, especially when the Smart Mattress is used during an evacuation procedure, where the underside (e.g., adjacent to where wheels may be located on a traditional Evacusled) may easily become damaged due to abrasions from transport. Due to the costs of mattresses, including the Smart Mattress, it would be advantageous to provide a replacement skin that a hospital could purchase for the Smart Mattress or Smart Mattress/Evacusled combo rather than having to buy an entirely new system.

The top skin and bottom skin panels may be zipped together and secured with a flap to form a continuous skin. In another embodiment, the skin may also include an intermediate side-wall skin between the top and bottom skin panels. The skin material should meet infection control measures and may also contain microclimate features. The replacement skins would retail for just a fraction of the cost of the Smart Mattress, therefore enhancing the life of the Smart Mattress and/or Evacusled.

The Smart Mattress and/or Evacusled should meet the demanding infection control measures which are essential in medical facilities. A solution to maintain an anti-fugal and anti-bacterial mattress surface would be to coat the mattress system with spray-on liquid glass. Spray-on liquid glass is transparent, non-toxic, and can protect virtually any surface against almost any damage from hazards such as water, UV radiation, dirt, heat, and bacterial infections. Liquid glass coating is also flexible and breathable, which makes it suitable for use on hospital mattresses.

Liquid glass spray (also referred to as "SiO2 ultra-thin layering") comprises almost pure silicon dioxide (silica, the normal compound in glass) extracted from quartz sand. Water or ethanol is added, depending on the type of surface to be coated. There are no additives, and the nano-scale glass coating bonds to the surface because of the quantum forces involved. Liquid glass has a long-lasting antibacterial effect because microbes landing on the surface cannot divide or replicate easily.

Liquid glass spray produces a water-resistant coating only around 100 nanometers (15-30 molecules) thick. On this nano-scale the glass is highly flexible and breathable. Liquid glass coating is environmentally harmless and non-toxic, and easy to clean using only water or a simple wipe with a damp cloth. It repels bacteria, water and dirt, and resists heat, UV light and even acids. Food processing companies in Germany have already carried out trials of the spray, and found sterile surfaces that usually needed to be cleaned with strong bleach to keep them sterile needed only a hot water rinse if they were coated with liquid glass. The levels of sterility were higher for the glass-coated surfaces, and the surfaces remained sterile for months. A year-long trial of the spray in a Lancashire hospital also produced very promising results for a range of applications including coatings for equipment, medical implants, catheters, sutures and bandages.

Since many patients spend a majority of their hospital stays on mattresses, and, depending on their conditions, may spend their entire lives confined to their beds, the Smart Mattress and Evacusled must combine the best practices of therapeutic mattress design.

Depending on the patient's need, there may be various Smart Mattress models. A standard Smart Mattress model may include a form mattress and Evacusled absent additional therapeutic features. A medical bed with air would integrate an air surface mattress to prevent pressure ulcers and may contain multiple independent zones of continuous low pressure to reduce the peak pressures that cause and aggravate skin ulcers. Yet another example may be a critical care design to be used in intensive care wards. A critical care design would be radiolucent or contain the x-ray cassette sleeve stated above. Additionally, a critical care mattress may have the most advanced therapeutic feather currently available in the marketplace (e.g., pressure redistribution surface, microclimate mattress surface to remove heat and moisture to cool the patient and keep the patient's skin drier, weight-based pressure sensors to distribute patient's weight, and a patient turn-assist feature to make it easy to change linens and conduct skin assessments on bed-ridden, critical care patients). Naturally, various combinations of these models may be made depending on the market's demand.

The Smart Mattress may also use a triage tag, which is particularly useful in emergency situations. Triage tags are tools that are often used for first responders and medical personnel use during a mass casualty incident. With the aid of the triage tags, the first-arriving personnel are able to effectively and efficiently distribute the limited resources and provide the necessary immediate care for the victims until more help arrives. Simple Triage and Rapid Treatment ("START") is a strategy that the first responders and medical personnel employ to evaluate the severity of injury of each victim as quickly as possible and tag a victim in about 30-60 seconds. The triage tags are placed near the head and are used to better separate the victims so that when more help arrives, the patients are easily recognizable for the extra help to ascertain the direst cases.

For the purpose of the Smart Mattress, Evacusled or combination Smart Mattress Evacusled design, the triage tags will preferably be placed on the foot-end of the mattress, so once the mattress is deployed, the triage tag is clearly visible. The triage tag may have a folding design allowing effective, quick and simple triage, but more importantly the folding tag allows patients to be re-triaged without having to replace the tag. This is in line with States that have standardized triage tags. Presently, the U.S. states and cities that use a standardized or Dynamic Triage Tag include New York, Connecticut, Indiana, Illinois, North Carolina, Nevada, Philadelphia, and Boston. The basic sections of a triage tag include four colors of triage including: Black (Expectant) which entails pain medication only until death; Red (Immediate) which entails life threatening injuries; Yellow (Delayed) which entails non-life threatening injuries; and Green (Minor) which entails minor injuries.

The triage tag may also include a section informing medical personnel of the patient's vital signs along with the treatment administered, a section on the patient's demographics (i.e., gender, residential address, etc. and the patient's medical history), and/or a section with a full pictorial view of the human body where the medical personnel may indicate which parts of the body are injured.

Although various embodiments have been described with reference to a particular arrangement of parts, features and the like, these are not intended to exhaust all possible arrangements or features, and indeed many other embodiments, modifications and variations will be ascertainable to those of skill in the art.

What is claimed is:

1. A mattress comprising:
   a sensor pad affixed on a top surface of the mattress, said sensor pad having a laminate,
   said laminate comprising:
   (i) a sensor substrate, which comprises a matrix array of plural pressure sensors,
   (ii) a row conductor substrate having plural row conductors, and
   (iii) a column conductor substrate having plural column conductors, said sensor substrate being disposed between the row conductor substrate and the column conductor substrate,
   wherein at least each one of the plural row conductors intersects with at least one of the plural row column conductors to provide an intersecting row and column conductor, each intersecting row and column conductor configured to provide an electrical signal from a corresponding pressure sensor when pressure is applied thereto,
   said sensor pad having plural flexibility-enhancing holes therein disposed between said plural row conductors and said plural column conductors, respectively, each flexibility-enhancing hole extending entirely through said laminate;
   at least one connector coupled to outputs of the row and column conductors; at least one patient-mounted physiological sensor configured to provide an output signal corresponding to a patient physiological parameter;
   an electronic unit mounted inside said mattress and having a panel mounted on a side of said mattress, said panel configured to receive signals from said at least one connector, said electronic unit having a data storage unit storing (i) patient identification information, (ii) patient physiological information, and (iii) mattress information, said electronic unit receiving signals from said at least one patient-mounted physiological sensor, said electronic unit having a processor; and
   a wireless transmitter coupled to said electronic unit and configured to wirelessly communicate at least the stored patient physiological information to an off-mattress device.

2. A mattress according to claim 1, wherein the sensor pad is disposed inside an envelope affixed to the top surface of the mattress.

3. A mattress according to claim 1, wherein the electronic unit includes a portable electrical energy source.

4. A mattress according to claim 1, wherein the wireless transmitter is configured to transmit via at least one of Bluetooth and WiFi.

5. A mattress according to claim 1, wherein said electronic unit includes a GPS device.

6. A mattress according to claim 1, wherein said electronic unit scans said plural row conductors and said plural column conductors, and provides a signal corresponding to a pressure map of the patient's body.

7. A mattress according to claim 1, further comprising a portable unit in communication with said wireless transmitter.

8. A mattress according to claim 1, further comprising a call button coupled to said electronic unit panel.

9. A mattress according to claim 1, wherein the sensor pad is configured to detect at least one of temperature and liquid.

10. A mattress according to claim 1, wherein said electronic unit is configured to detect respiration based on outputs of said sensor pad.

11. A mattress according to claim 1, wherein said electronic unit is configured to detect heart beat based on outputs of said sensor pad.

12. A mattress according to claim 1, wherein said electronic unit is configured to provide an alarm signal whenever a monitored physiological parameter exceeds a predetermined threshold.

* * * * *